United States Patent
Busch-Petersen et al.

(10) Patent No.: US 7,276,521 B2
(45) Date of Patent: Oct. 2, 2007

(54) MUSCARINIC ACETYLCHOLINE RECEPTOR ANTAGONISTS

(75) Inventors: Jakob Busch-Petersen, King of Prussia, PA (US); Michael R. Palovich, King of Prussia, PA (US); Zehong Wan, King of Prussia, PA (US); Hongxing Yan, King of Prussia, PA (US); Chongjie Zhu, King of Prussia, PA (US)

(73) Assignee: Glaxo Group Limited, Greenford, Middlesex (GB)

( * ) Notice: Subject to any disclaimer, the term of this patent is extended or adjusted under 35 U.S.C. 154(b) by 0 days.

(21) Appl. No.: 10/575,839

(22) PCT Filed: Oct. 12, 2004

(86) PCT No.: PCT/US2004/033638

§ 371 (c)(1),
(2), (4) Date: Apr. 13, 2006

(87) PCT Pub. No.: WO2005/037280

PCT Pub. Date: Apr. 28, 2005

(65) Prior Publication Data

US 2007/0105895 A1    May 10, 2007

Related U.S. Application Data

(60) Provisional application No. 60/511,009, filed on Oct. 14, 2003.

(51) Int. Cl.
| | |
|---|---|
| A01N 43/42 | (2006.01) |
| A61K 31/44 | (2006.01) |
| C07D 451/02 | (2006.01) |
| C07D 401/00 | (2006.01) |
| C07D 405/00 | (2006.01) |

(52) U.S. Cl. .................. 514/304; 546/124; 546/125

(58) Field of Classification Search .............. 546/124, 546/125; 514/304
See application file for complete search history.

(56) References Cited

U.S. PATENT DOCUMENTS

| | | | |
|---|---|---|---|
| 2,800,478 | A | 7/1957 | Zickle et al. |
| 2,800,481 | A | 7/1957 | Zickle et al. |
| 2,800,482 | A * | 7/1957 | Zirkle .................. 546/124 |
| 6,248,752 | B1 | 6/2001 | Smith |
| 6,262,066 | B1 | 7/2001 | Tulshian et al. |
| 6,350,758 | B1 | 2/2002 | Kozikowski et al. |
| 6,455,527 | B2 | 9/2002 | Tulshian et al. |
| 2006/0160844 | A1 | 7/2006 | Belmonte et al. |
| 2006/0178395 | A1 | 8/2006 | Belmonte et al. |
| 2006/0178396 | A1 | 8/2006 | Belmonte et al. |
| 2006/0211758 | A1 | 9/2006 | Busch-Peterson et al. |

FOREIGN PATENT DOCUMENTS

| | | |
|---|---|---|
| WO | 2004/012684 | 2/2004 |
| WO | 2006/050239 | 5/2006 |
| WO | 2006/055503 | 5/2006 |
| WO | 2006/055553 | 5/2006 |
| WO | 2006/062883 | 6/2006 |
| WO | 2006/062931 | 6/2006 |
| WO | 2006/065755 | 6/2006 |
| WO | 2006/065788 | 6/2006 |
| WO | 2007/016639 | 2/2007 |
| WO | 2007/016650 | 2/2007 |
| WO | 2007/018508 | 2/2007 |
| WO | 2007/018514 | 2/2007 |
| WO | 2007/022351 | 2/2007 |

OTHER PUBLICATIONS

The Muscarinic Receptors (The Receptors). Brown, Joan Heller; Editor. USA. (1989), 478 pp. Publisher: (Humana Press, Clifton, N.J.).
Costello, Richard W.; Evans, Christopher M.; Yost, Bethany L.; Belmonte, Kristen E.; Gleich, Gerald J.; Jacoby, David B.; Fryer, Allison D. Antigen-induced hyperreactivity to histamine: role of the vagus nerves and eosinophils. American Journal of Physiology (1999), 276(5, Pt. 1), L709-L714.
Minette P A; Lammers J W; Dixon C M; McCusker M T; Barnes P J A muscarinic agonist inhibits reflex bronchoconstriction in normal but not in asthmatic subjects. Journal of applied physiology (Bethesda, Md. : 1985) (1989), 67(6), 2461-5.
Oprins, Judith C. J.; Meijer, Helen P.; Groot, Jack A. Tumor necrosis factor-a potentiates ion secretion induced by muscarinic receptor activation in the human intestinal epithelial cell line HT29cl.19A. Annals of the New York Academy of Sciences (2000), 915(Epithelial Transport and Barrier Function), 102-106.
Hegde, Sharath S.; Eglen, Richard M. Muscarinic receptor subtypes modulating smooth muscle contractility in the urinary bladder. Life Sciences (1999), 64(6/7), 419-428.
The Muscarinic Receptors (The Receptors), *History and Basic Properties*, pp. 7-9. Brown, Joan Heller; Editor. USA. (1989), Publisher: (Humana Press, Clifton, N.J.).
Zirkle, et al., *J Med Chem*, vol. 5 pp. 341-356 (1962).
Wu, et al., *Zhongguo Yaowu Huazue Zazhi*, vol. 3 (1) pp. 23-26 (1993)ABSTRACT only.
Ran, et al., *Yaoxue Xuebao*, vol. 19 (5) pp. 361-366 (1984) ABSTRACT only.
Ikeda, et al., *Naunyn-Schmiedeberg's Arch Pharmacol.*, vol. 366, pp. 97-103, (2002).
Caulfield, *Pharmac. Ther.*, vol. 58 pp. 319-379 (1993).
Fryer and Jacoby, *Am J Respir Crit Care Med*, vol. 158 (5, pt 3) pp. 154-160 (1998).
Fryer et al., *Life Sci*, vol. 64 (6-7) pp. 449-455 (1999).
Pauwels et al., *Am. J. Respir. Crit. Care Med.*, vol. 163 pp. 1256-1276 (2001).
U.S. Appl. No. 10/598,888, filed Sep. 14, 2006, Busch-Peterson et al.
U.S. Appl. No. 10/598,887, filed Sep. 14, 2006, Busch-Peterson et al.
U.S. Appl. No. 10/598,885, filed Sep. 14, 2006, Busch-Peterson et al.
U.S. Appl. No. 10/598,882, filed Sep. 14, 2006, Busch-Peterson et al.
U.S. Appl. No. 10/599,717, filed Oct. 6, 2006, Laine et al.
U.S. Appl. No. 11/568,330, filed May 3, 2007, Laine et al.
U.S. Appl. No. 11/568,930, filed Nov. 10, 2006, Laine et al.
U.S. Appl. No. 11/568,909, filed Nov. 10, 2006, Palovich et al.
U.S. Appl. No. 11/570,981, filed Dec. 20, 2006, Cooper et al.
U.S. Appl. No. 11/573,097, filed Feb. 2, 2007, Busch-Peterson et al.
U.S. Appl. No. 11/573,099, filed Feb. 2, 2007, Busch-Peterson et al.

* cited by examiner

*Primary Examiner*—Margaret D. Seaman
*Assistant Examiner*—Niloofar Rahmani
(74) *Attorney, Agent, or Firm*—Mary E. McCarthy; Charles M. Kinzig

(57) ABSTRACT

Muscarinic Acetylcholine Receptor Antagonists and methods of using them are provided.

32 Claims, No Drawings

MUSCARINIC ACETYLCHOLINE RECEPTOR ANTAGONISTS

This application is the §371 national stage entry of PCT/US2004/033638, filed 12 Oct. 2004 which claims the benefit of priority of U.S. Provisional Application No. 60/511,009 filed 14 Oct., 2003.

FIELD OF THE INVENTION

This invention relates to novel derivatives of 8-azoniabicyclo[3,2,1]octanes, pharmaceutical compositions, processes for their preparation, and use thereof in treating $M_3$ muscarinic acetylcholine receptor mediated diseases.

BACKGROUND OF THE INVENTION

Acetylcholine released from cholinergic neurons in the peripheral and central nervous systems affects many different biological processes through interaction with two major classes of acetylcholine receptors—the nicotinic and the muscarinic acetylcholine receptors. Muscarinic acetylcholine receptors (mAChRs) belong to the superfamily of G-protein coupled receptors that have seven transmembrane domains. There are five subtypes of mAChRs, termed $M_1$-$M_5$, and each is the product of a distinct gene. Each of these five subtypes displays unique pharmacological properties. Muscarinic acetylcholine receptors are widely distributed in vertebrate organs, and these receptors can mediate both inhibitory and excitatory actions. For example, in smooth muscle found in the airways, bladder and gastrointestinal tract, $M_3$ mAChRs mediate contractile responses. For review, please see {Brown 1989 247/id}.

Muscarinic acetylcholine receptor dysfunction has been noted in a variety of different pathophysiological states. For instance, in asthma and chronic obstructive pulmonary disease (COPD), inflammatory conditions lead to loss of inhibitory $M_2$ muscarinic acetylcholine autoreceptor function on parasympathetic nerves supplying the pulmonary smooth muscle, causing increased acetylcholine release following vagal nerve stimulation. This mAChR dysfunction results in airway hyperreactivity mediated by increased stimulation of $M_3$ mAChRs {Costello, Evans, et al. 1999 72/id} {Minette, Lammers, et al. 1989 248/id}. Similarly, inflammation of the gastrointestinal tract in inflammatory bowel disease (IBD) results in $M_3$ mAChR-mediated hypermotility {Oprins, Meijer, et al. 2000 245/id}. Incontinence due to bladder hypercontractility has also been demonstrated to be mediated through increased stimulation of $M_3$ mAChRs {Hegde & Eglen 1999 251/id}. Thus the identification of subtype-selective mAChR antagonists may be useful as therapeutics in these mAChR-mediated diseases.

Despite the large body of evidence supporting the use of anti-muscarinic receptor therapy for treatment of a variety of disease states, relatively few anti-muscarinic compounds are in use in the clinic. Thus, there remains a need for novel compounds that are capable of causing blockade at $M_3$ mAChRs. Conditions associated with an increase in stimulation of $M_3$ mAChRs, such as asthma, COPD, IBD and urinary incontinence would benefit by compounds that are inhibitors of mAChR binding.

SUMMARY OF THE INVENTION

This invention provides for a method of treating a muscarinic acetylcholine receptor (mAChR) mediated disease, wherein acetylcholine binds to an $M_3$ mAChR and which method comprises administering an effective amount of a compound of Formula (I) or Formula (II) [except the compound of Formula (II) with R2 and R3 as 2-thiophene and R4 as —OC(O)CH₃] or a pharmaceutically acceptable salt thereof.

This invention also relates to a method of inhibiting the binding of acetylcholine to its receptors in a mammal in need thereof which comprises administering to aforementioned mammal an effective amount of a compound of Formula (I) or Formula (II).

The present invention also provides for the novel compounds of Formula (I) or Formula (II), and pharmaceutical compositions comprising a compound of Formula (I) or Formula (II), and a pharmaceutical carrier or diluent.

Compounds of Formula (I) or Formula (II) useful in the present invention are represented by the structure:

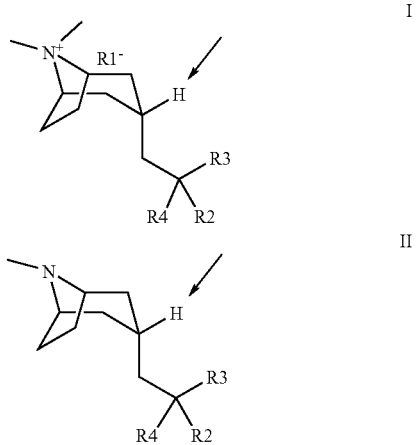

wherein:

the H atom indicated is in the exo position;

R1⁻ represents an anion associated with the positive charge of the N atom. R1⁻ may be but is not limited to chloride, bromide, iodide, sulfate, benzene sulfonate and toluene sulfonate;

R2 and R3 are independently selected from the group consisting of straight or branched chain lower alkyl groups (having preferably from 1 to 6 carbon atoms), cycloalkyl groups (having from 5 to 6 carbon atoms), cycloalkyl-alkyl (having 6 to 10 carbon atoms), heterocycloalkyl (having 5 to 6 carbon atoms) and N or O as the heteroatom, heterocycloalkyl-alkyl (having 6 to 10 carbon atoms) and N or O as the heteroatom, aryl, optionally substituted aryl, heteroaryl, and optionally substituted heteroaryl;

R4 is selected from the group consisting of $(C_1-C_6)$alkyl, $(C_3-C_7)$cycloalkyl, $(C_3-C_7)$heterocycloalkyl, $(C_1-C_6)$alkyl$(C_3-C_{12})$cycloalkyl, $(C_1-C_6)$alkyl$(C_3-C_7)$heterocycloalkyl, aryl, heteroaryl, $(C_1-C_6)$alkyl-aryl, $(C_1-C_6)$alkyl-heteroaryl, —OR5, —CH₂OR5, —CH₂OH, —CN, —CF₃, —CH₂O(CO)R6, —CO₂R7, —CH₂NH₂, —CH₂N(R7)SO₂R5, —SO₂N(R7)(R8), —CON(R7)(R8), —CH₂N(R8)CO(R6), —CH₂N(R8)SO₂(R6), —CH₂N(R8)CO₂(R5), —CH₂N(R8)CONH(R7);

R5 is selected from the group consisting of $(C_1-C_6)$alkyl, $(C_1-C_6)$alkyl$(C_3-C_{12})$cycloalkyl, $(C_1-C_6)$alkyl$(C_3-C_7)$heterocycloalkyl, $(C_1-C_6)$alkyl-aryl, $(C_1-C_6)$alkyl-heteroaryl;

R6 is selected from the group consisting of $(C_1-C_6)$alkyl, $(C_3-C_{12})$cycloalkyl, $(C_3-C_7)$heterocycloalkyl, $(C_1-C_6)$ alkyl($C_3$-$C_{12}$)cycloalkyl, ($C_1$-$C_6$)alkyl($C_3$-$C_7$)heterocycloalkyl, aryl, heteroaryl, ($C_1$-$C_6$)alkyl-aryl, ($C_1$-$C_6$) alkyl-heteroaryl;

R7 and R8 are, independently, selected from the group consisting of H, ($C_1$-$C_6$)alkyl, ($C_3$-$C_{12}$)cycloalkyl, ($C_3$-$C_7$)heterocycloalkyl, ($C_1$-$C_6$)alkyl($C_3$-$C_{12}$)cycloalkyl, ($C_1$-$C_6$)alkyl($C_3$-$C_7$)heterocycloalkyl, ($C_1$-$C_6$)alkyl-aryl, and ($C_1$-$C_6$)alkyl-heteroaryl.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of Formula (I) or Formula (II) may also be formed with a pharmaceutically acceptable cation. Suitable pharmaceutically acceptable cations are well known to those skilled in the art and include alkaline, alkaline earth, ammonium and quaternary ammonium cations.

The following terms, as used herein, refer to:

"halo"—all halogens, that is chloro, fluoro, bromo and iodo.

"$C_{1-10}$alkyl" or "alkyl"—both straight and branched chain moieties of 1 to 10 carbon atoms, unless the chain length is otherwise limited, including, but not limited to, methyl, ethyl, n-propyl, iso-propyl, n-butyl, sec-butyl, iso-butyl, tert-butyl, n-pentyl and the like.

"cycloalkyl" is used herein to mean cyclic moiety, preferably of 3 to 8 carbons, including but not limited to cyclopropyl, cyclopentyl, cyclohexyl, and the like.

"alkenyl" is used herein at all occurrences to mean straight or branched chain moiety of 2-10 carbon atoms, unless the chain length is limited thereto, including, but not limited to ethenyl, 1-propenyl, 2-propenyl, 2-methyl-1-propenyl, 1-butenyl, 2-butenyl and the like.

"aryl"—phenyl and naphthyl;

"heteroaryl" (on its own or in any combination, such as "heteroaryloxy", or "heteroaryl alkyl")—a 5-10 membered aromatic ring system in which one or more rings contain one or more heteroatoms selected from the group consisting of N, O or S, such as, but not limited, to pyrrole, pyrazole, furan, thiophene, quinoline, isoquinoline, quinazolinyl, pyridine, pyrimidine, oxazole, tetrazole, thiazole, thiadiazole, triazole, imidazole, or benzimidazole.

"heterocyclic" (on its own or in any combination, such as "heterocyclicalkyl") —a saturated or partially unsaturated 4-10 membered ring system in which one or more rings contain one or more heteroatoms selected from the group consisting of N, O, or S; such as, but not limited to, pyrrolidine, piperidine, piperazine, morpholine, tetrahydropyran, thiomorpholine, or imidazolidine. Furthermore, sulfur may be optionally oxidized to the sulfone or the sulfoxide.

"arylalkyl" or "heteroarylalkyl" or "heterocyclicalkyl" is used herein to mean $C_{1-10}$ alkyl, as defined above, attached to an aryl, heteroaryl or heterocyclic moiety, as also defined herein, unless otherwise indicated.

"sulfinyl"—the oxide S(O) of the corresponding sulfide, the term "thio" refers to the sulfide, and the term "sulfonyl" refers to the fully oxidized S(O)$_2$ moiety.

"wherein two R$_1$ moieties (or two Y moieties) may together form a 5 or 6 membered saturated or unsaturated ring" is used herein to mean the formation of an aromatic ring system, such as naphthalene, or is a phenyl moiety having attached a 6 membered partially saturated or unsaturated ring such as a $C_6$ cycloalkenyl, i.e. hexene, or a $C_5$ cycloalkenyl moiety, such as cyclopentene.

Preferred compounds useful in the present invention include:

(Endo)-3-(2-methoxy-2,2-di-thiophen-2-yl-ethyl)-8,8-dimethyl-8-azonia-bicyclo[3.2.1]octane iodide;

3-((Endo)-8-methyl-8-aza-bicyclo[3.2.1]oct-3-yl)-2,2-diphenyl-propionitrile;

(Endo)-8-methyl-3-(2,2,2-triphenyl-ethyl)-8-aza-bicyclo[3.2.1]octane;

3-((Endo)-8-methyl-8-aza-bicyclo[3.2.1]oct-3-yl)-2,2-diphenyl-propionamide;

3-((Endo)-8-methyl-8-aza-bicyclo[3.2.1]oct-3-yl)-2,2-diphenyl-propionic acid;

(Endo)-3-(2-cyano-2,2-diphenyl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane bromide;

3-((Endo)-8-methyl-8-aza-bicyclo[3.2.1]oct-3-yl)-2,2-diphenyl-propan-1-ol;

N-Benzyl-3-((endo)-8-methyl-8-aza-bicyclo[3.2.1]oct-3-yl)-2,2-diphenyl-propionamide;

(Endo)-3-(2-carbamoyl-2,2-diphenyl-ethyl)-8,8-dimethyl-8-azonia-bicyclo[3.2.1]octane iodide;

1-Benzyl-3-[3-((endo)-8-methyl-8-aza-bicyclo[3.2.1]oct-3-yl)-2,2-diphenyl-propyl]-urea;

1-Ethyl-3-[3-((endo)-8-methyl-8-aza-bicyclo[3.2.1]oct-3-yl)-2,2-diphenyl-propyl]-urea;

N-[3-((Endo)-8-methyl-8-aza-bicyclo[3.2.1]oct-3-yl)-2,2-diphenyl-propyl]-acetamide;

N-[3-((Endo)-8-methyl-8-aza-bicyclo[3.2.1]oct-3-yl)-2,2-diphenyl-propyl]-benzamide;

3-((Endo)-8-methyl-8-aza-bicyclo[3.2.1]oct-3-yl)-2,2-di-thiophen-2-yl-propionitrile;

(Endo)-3-(2-cyano-2,2-di-thiophen-2-yl-ethyl)-8,8-dimethyl-8-azonia-bicyclo[3.2.1]octane iodide;

N-[3-((Endo)-8-methyl-8-aza-bicyclo[3.2.1]oct-3-yl)-2,2-diphenyl-propyl]-benzenesulfonamide;

[3-((Endo)-8-methyl-8-aza-bicyclo[3.2.1]oct-3-yl)-2,2-diphenyl-propyl]-urea;

N-[3-((Endo)-8-methyl-8-aza-bicyclo[3.2.1]oct-3-yl)-2,2-diphenyl-propyl]-methanesulfonamide; and (Endo)-3-{2,2-diphenyl-3-[(1-phenyl-methanoyl)-amino]-propyl}-8,8-dimethyl-8-azonia-bicyclo[3.2.1]octane bromide.

More preferred compounds useful in the present invention include:

(Endo)-3-(2-methoxy-2,2-di-thiophen-2-yl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane iodide;

(Endo)-3-(2-cyano-2,2-diphenyl-ethyl)-8,8-dimethyl-8-azonia-bicyclo[3.2.1]octane bromide;

(Endo)-3-(2-carbamoyl-2,2-diphenyl-ethyl)-8,8-dimethyl-8-azonia-bicyclo[3.2.1]octane iodide;

(Endo)-3-(2-cyano-2,2-di-thiophen-2-yl-ethyl)-8,8-dimethyl-8-azonia-bicyclo[3.2.1]octane iodide; and (Endo)-3-{2,2-diphenyl-3-[(1-phenyl-methanoyl)-amino]-propyl}-8,8-dimethyl-8-azonia-bicyclo[3.2.1]octane bromide.

Methods of Preparation

Preparation

The compounds of Formula (I) and Formula (II) may be obtained by applying synthetic procedures, some of which are illustrated in the Schemes below. The synthesis provided for these Schemes is applicable for producing compounds of Formula (I) and Formula (II) having a variety of different R1, R2, R3 and R4 which are reacted, employing substituents which are suitable protected, to achieve compatibility with the reactions outlined herein. Subsequent deprotection, in those cases, then affords compounds of the nature generally disclosed. While some schemes are shown with compounds only of Formula (II), this is merely for illustration purpose only.

The general preparation method is shown in Scheme I. The synthesis started with compound 1. Reduction with lithium aluminium hydride (LAH) afforded alcohol 2. Displacement with iodine provided 3. Coupling reaction with the anion derived from HCR2(R3)(R4) then furnished compound 4, which was easily converted to ammonium salt 5.

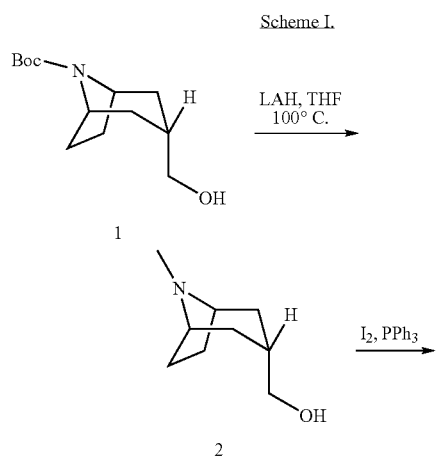

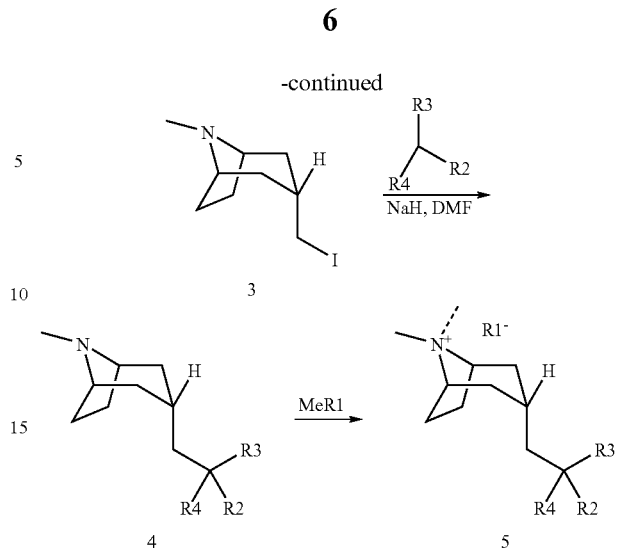

A more specific preparation method leading to compounds with Formula (II) is outlined in Scheme II. Alkylation of ester $HC(Ph)_2CO_2CH_3$ with 3 afforded compound 6. Hydrolysis of 6 generated acid 7. 1,3-Dicyclohexylcarbodiimide (DCC) mediated condensation of the acid with alcohol (R7)OH then furnished ester 8. Condensation of acid 7 with amine (R7)(R8)NH under suitable amide coupling conditions well known to those skilled in the art such as 1-(3-dimethylaminopropyl)-3-ethylcarbodiimide hydrochloride (EDC.HCl) and 1-hydroxybenzotriazole hydrate (HOBt) provided amide 9. Reduction of 6 generated alcohol 10. Reaction of 10 with acid chloride (R6)COCl or acid (R6)$CO_2H$ afforded ester 11. Alkylation of 10 with appropriate reagents such as (R5)Br then furnished 12.

Compounds with structures similar to 6, 7, 8, 9, 10, 11 and 12 were converted to corresponding ammonium salts by reacting with appropriate reaction reagents such as MeBr and MeI (not shown in the scheme). Appropriate protection and deprotection methods were utilized in some preparation procedures.

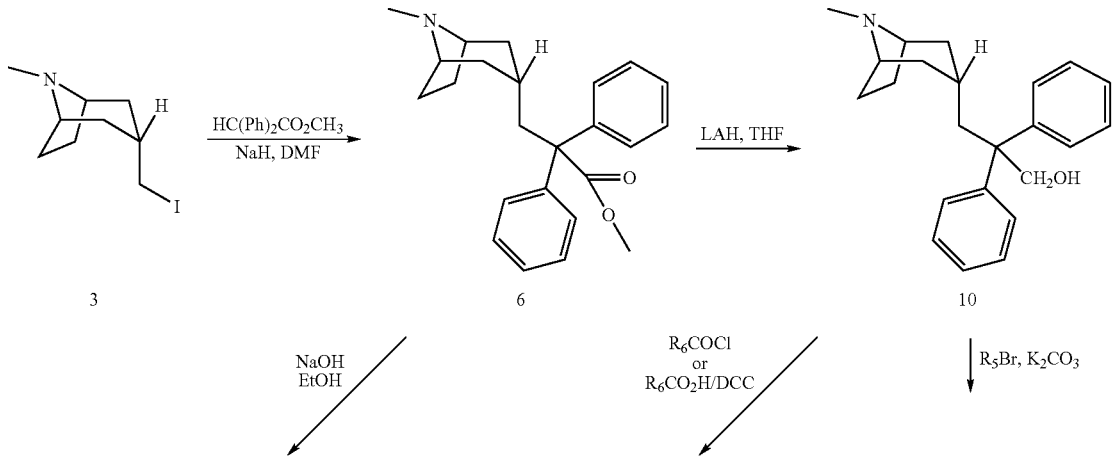

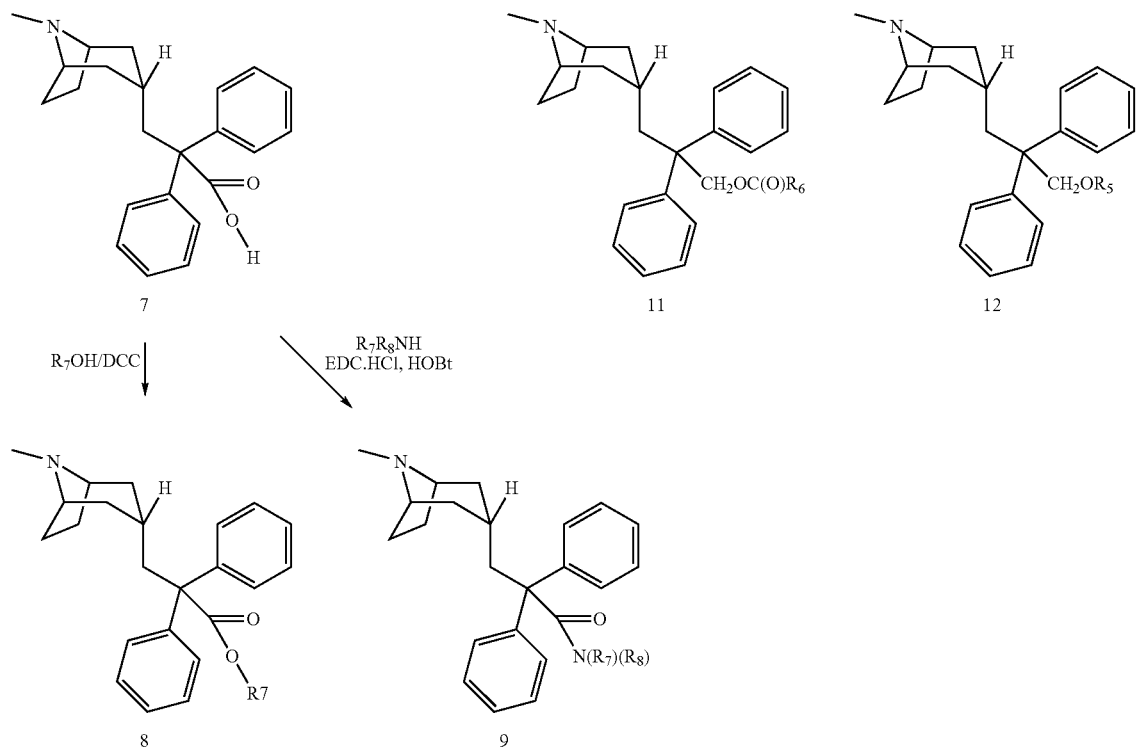

A more specific preparation method leading to compounds with Formula (II) is outlined in Scheme III. Alkylation of HC(Ph)$_2$CN with 3 provided nitrile 13. Hydrolysis of 13 under either basic conditions (e.g., NaOH and H$_2$O$_2$) or acidic conditions (e.g., H$_2$SO$_4$) afforded amide 14. Reduction of 13 led to amine 15 that was conveniently transformed to amide 16, carbamide 17, sulfonamide 18 and urea 19. Condensation of 15 with aldehyde (R8)CH(O) followed by reduction with NaBH(OAc)$_3$ furnished amine 20 that was easily converted to amide 21, carbamide 22, urea 23 and sulfonamide 24.

Compounds with structures similar to 13, 14, 15, 16, 17, 18, 19, 20, 21, 22, 23 and 24 were converted to corresponding ammonium salts by reacting with appropriate reaction reagents such as MeBr and MeI (not shown in the scheme). Appropriate protection and deprotection methods were utilized in some preparation procedures.

SCHEME III.

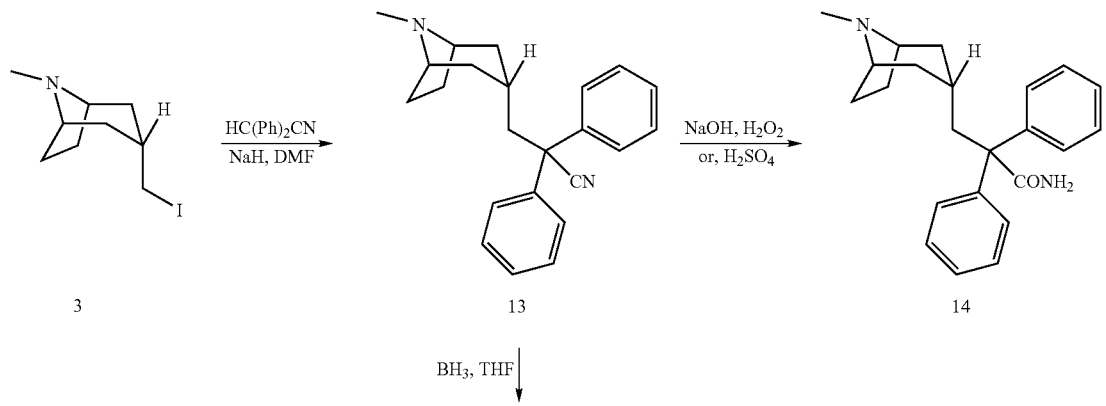

-continued

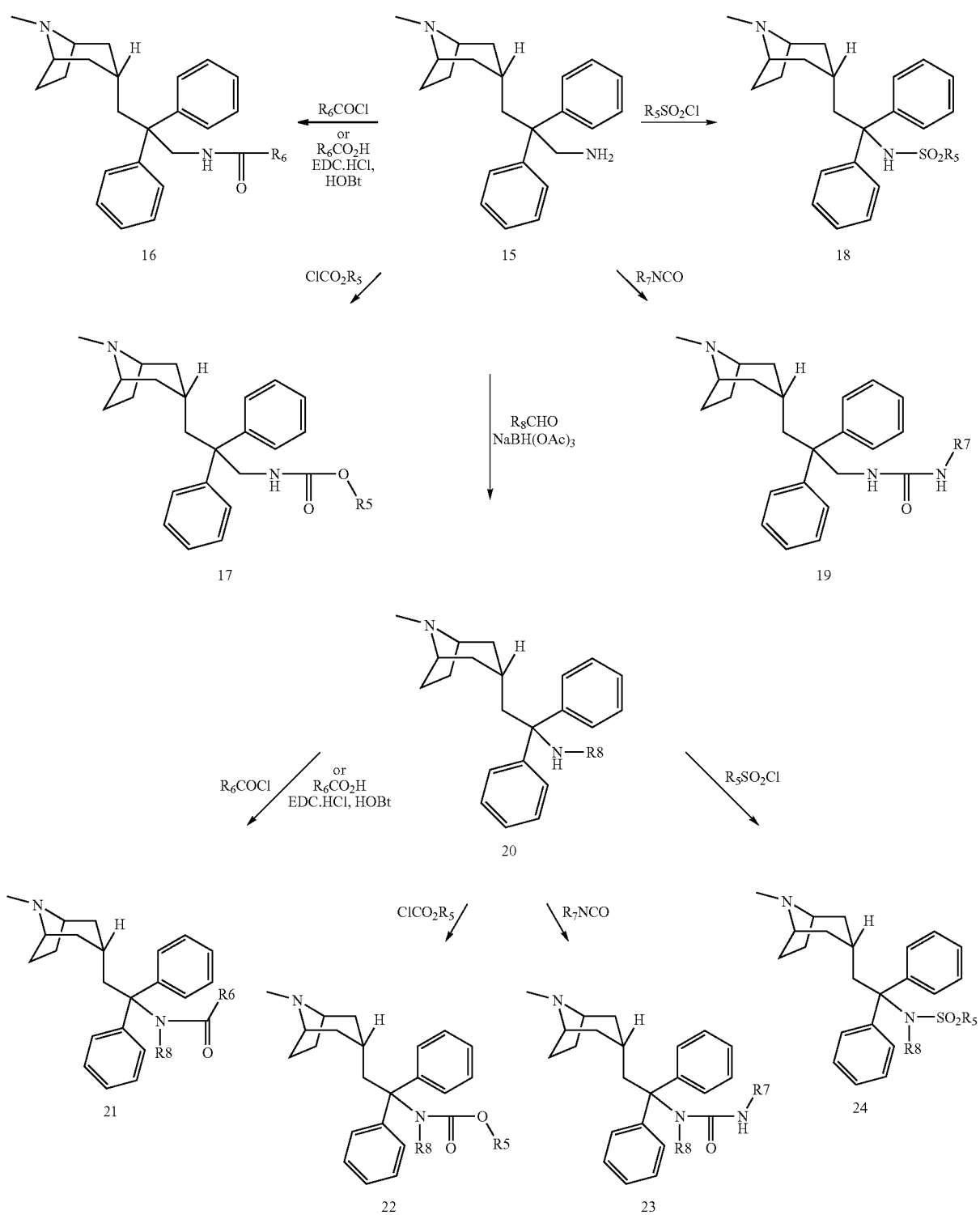

A more specific preparation method leading to compounds with Formula (II) is outlined in Scheme IV. Alkylation of 25 with (R5)Br provided 26. Reaction of 25 with Lawesson's reagent afforded 27. Oxidation of 27 with $SO_2Cl_2$ and $KNO_3$ furnished 28 that was converted to either 29 or sulfonamide 30.

Compounds with structures similar to 26, 27, 29 and 30 were easily converted to the corresponding ammonium salts by reacting with appropriate reaction reagents such as MeBr and MeI (not shown in the scheme). Appropriate protection and deprotection methods were utilized in some preparation procedures.

Scheme IV.

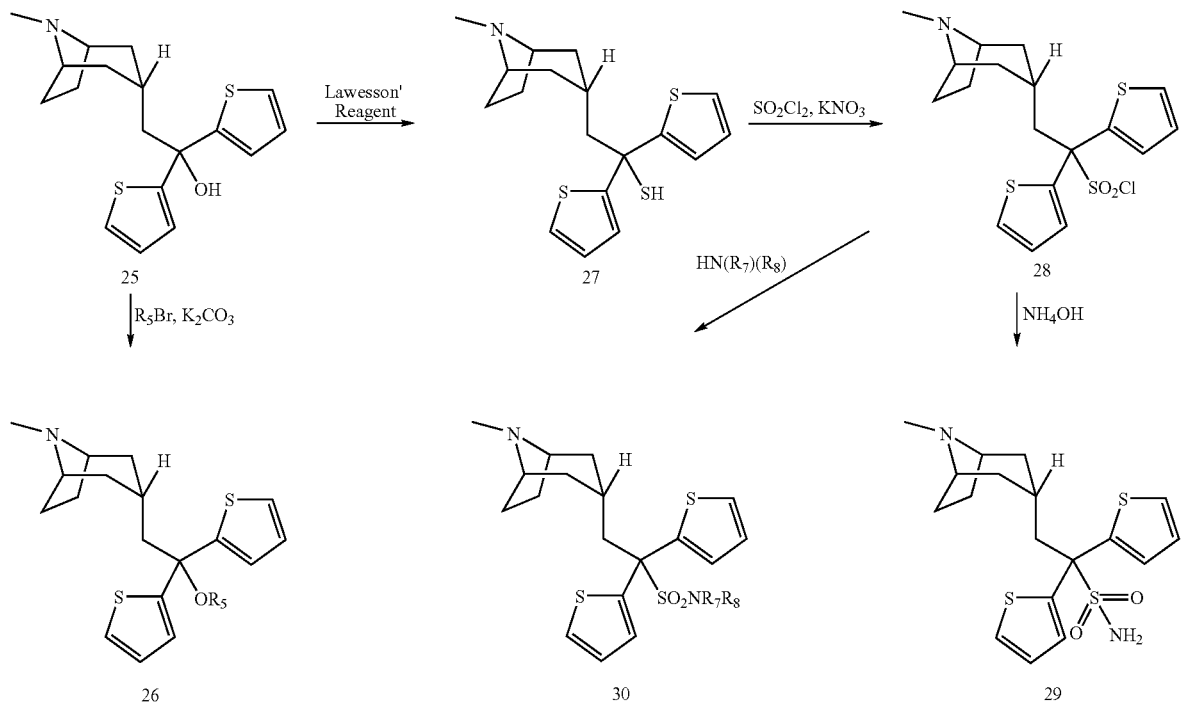

SYNTHETIC EXAMPLES

The following examples are provided as illustrative of the present invention but not limiting in any way:

Example 1

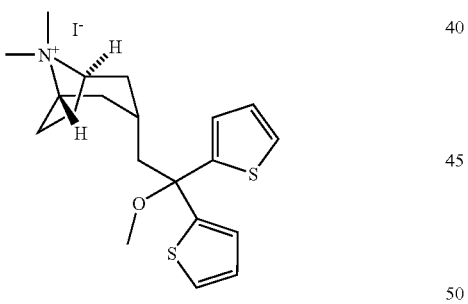

(Endo)-3-(2-methoxy-2,2-di-thiophen-2-yl-ethyl)-8,8-dimethyl-8-azonia-bicyclo[3.2.1]octane iodide To a solution of 2-(8-methyl-8-azabicyclo[3.2.1]oct-3-yl)-1,1-dithiophen-2-yl-ethanol (prepared according to U.S. Pat. No. 2,800,482) (212 mg, 0.64 mmol) in 5 mL methylenechloride and iodomethane (0.40 mL, 6.4 mmol), 50% aqueous potassium hydroxide (0.25 mL, 3.2 mmol) and tetrabutylammonium chloride (5 mg, 3 mol %) was added. The reaction mixture was heated to reflux for 5 d. Each day, an additional 0.2 mL iodomethane and 0.1 mL potassium hydroxide was added. Upon completion, the reaction mixture was cooled to room temperature, diluted with methylenechloride and washed with water. The aqueous layer was extracted with methylenechloride and the combined organic layers were washed with brine, dried over MgSO$_4$ and concentrated in vacuo. The crude product was recrystallized from methylenechloride/ethyl acetate to give 109 mg of the title compound: LCMS (ES) m/z 362 (M)$^+$.

Example 2

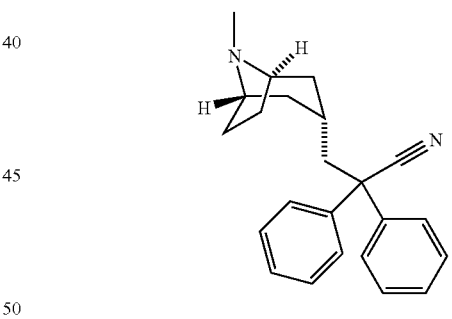

3-((Endo)-8-methyl-8-aza-bicyclo[3.2.1]oct-3-yl)-2,2-diphenyl-propionitrile

2a) Preparation of ((endo)-8-methyl-8-aza-bicyclo[3.2.1]oct-3-yl)-methanol

A mixture of 1,1-dimethylethyl (endo)-3-(hydroxymethyl)-8-azabicyclo[3.2.1]octane-8-carboxylate (0.50 g, 2.05 mmol) and LiAlH$_4$ (6.16 mL, 1.0 M in THF, 6.16 mmol) was heated at 80° C. with a microwave reactor for 60 min. The solution was then mixed with saturated Na$_2$SO$_4$ solution, filtered through celite and concentrated to afford the title compound (0.31 g, 97%): LCMS (ES) m/z 156 (M+H)$^+$; $^1$H-NMR(CDCl$_3$) δ 1.28 (s, 1H), 1.59 (m, 4H), 1.90 (m, 1H), 2.13 (m, 4H), 2.32 (s, 3H), 3.17 (s, 2H), 3.59 (d, 2H).

2b) Preparation of (endo)-3-iodomethyl-8-methyl-8-aza-bicyclo[3.2.1]octane

A solution of iodine (6.67 g, 25.8 mmol) and ((endo)-8-methyl-8-aza-bicyclo[3.2.1]oct-3-yl)-methanol (2.0 g, 12.9 mmol) in $CH_2Cl_2$ (120 mL) was mixed with $PPh_3$ (on resin, 8.6 g, 3 mmol/g, 25.8 mmol). The resultant mixture was stirred for 17 hours, filtered and concentrated to afford the title compound (2.63 g, 77%): LCMS (ES) m/z 266 (M+H)$^+$; $^1$H-NMR(CDCl$_3$) δ 2.05 (m, 4H), 2.39 (m, 3H), 2.79 (d, 3H), 2.98 (m, 2H), 3.45 (d, 2H), 3.81 (s, 2H).

2c) Preparation of 3-((endo)-8-methyl-8-aza-bicyclo[3.2.1]oct-3-yl)-2,2-diphenyl-propionitrile A solution of (endo)-3-iodomethyl-8-methyl-8-aza-bicyclo[3.2.1]octane (1.06 g, 4.0 mmol) and $PH_2CHCN$ (2.32 g, 12.0 mmol) in DMF (20 mL) was mixed with NaH (0.288 g, 12.0 mmol). The resultant mixture was stirred at room temperature for 60 minutes. Filtration and purification via a reverse phase HPLC (Gilson) then afforded the title compound (1.16 g, 93%): LCMS (ES) m/z 331 (M+H)$^+$; $^1$H-NMR(CDCl$_3$) δ 1.64 (m, 2H), 2.14 (m, 1H), 2.26 (m, 2H), 2.34 (m, 2H), 2.52 (m, 2H), 2.75 (m, 5H), 3.83 (s, 2H), 7.39 (d, 10H).

Example 3

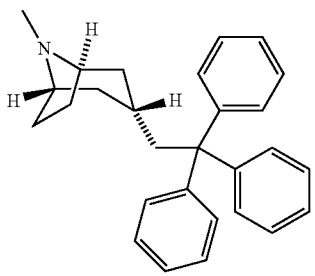

(Endo)-8-methyl-3-(2,2,2-triphenyl-ethyl)-8-aza-bicyclo[3.2.1]octane

A solution of triphenylmethane (0.276 g, 1.13 mmol) in THF (0.5 mL) was mixed with n-BuLi (0.706 mL, 1.6 M in Hexane, 1.13 mmol). The solution was stirred for 10 minutes and added by a solution of (endo)-3-iodomethyl-8-methyl-8-aza-bicyclo[3.2.1]octane (100 mg, 0.377 mmol) in DMF (1.0 mL). The mixture was stirred at room temperature for 60 minutes, mixed with $H_2O$ (0.1 mL), concentrated and filtered. Purification via a reverse phase HPLC (Gilson) then afforded the title compound (23.8 mg, 17%): LCMS (ES) m/z 382 (M+H)$^+$; $^1$H-NMR(CDCl$_3$) δ 1.07 (d, 2H), 2.12 (m, 1H), 2.22 (m, 4H), 2.31 (m, 2H), 2.65 (d, 3H), 2.97 (d, 2H), 3.63 (s, 2H), 7.21 (m, 3H), 7.30 (d, 12H).

Example 4

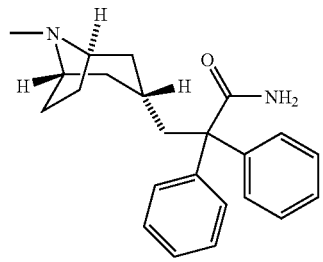

3-((Endo)-8-methyl-8-aza-bicyclo[3.2.1]oct-3-yl)-2,2-diphenyl-propionamide

A solution of 3-((endo)-8-methyl-8-aza-bicyclo[3.2.1]oct-3-yl)-2,2-diphenyl-propionitrile (53 mg, 0.16 mmol) in $CH_2Cl_2$ (0.25 mL) was mixed with $H_2SO_4$ (0.28 mL, 96%) and stirred at 40° C. for 30 hours. The mixture was then poured into ice, neutralized with $NH_3.H_2O$, extracted with EtOAc and concentrated. The resultant residue was dissolved in DMSO and filtered. Purification via a reverse phase HPLC (Gilson) provided the title compound (17.2 mg, 30%): MS (ES) m/z 347 (M+H)$^+$; $^1$H-NMR(CDCl$_3$) δ 1.31 (d, 2H), 1.98 (m, 1H), 2.28 (m, 4H), 2.39 (m, 2H), 2.67 (d, 3H), 2.79 (d, 2H), 3.66 (s, 2H), 5.82 (s, br, 1H), 6.88 (s, br, 1H), 7.37 (m, 10H).

Example 5

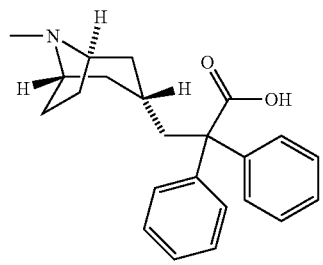

3-((Endo)-8-methyl-8-aza-bicyclo[3.2.1]oct-3-yl)-2,2-diphenyl-propionic acid

A solution of 2-[(3-endo)-8-methyl-8-azabicyclo[3.2.1]oct-3-yl]-1,1-diphenylethanol (100 mg, 1.56 mmol) in HCOOH (0.25 mL) was quickly added by $H_2SO_4$ (2.73 mL, 90%) at 0° C. The reaction vial was capped immediately and stored in a refrigerator at −20° C. for 7 days. The solution was poured into ice, neutralized with $NH_3.H_2O$, extracted with EtOAc and concentrated. The resultant residue was dissolved in DMSO and filtered. Purification via a reverse phase HPLC (Gilson) then afforded the title compound (52 mg, 48%): LCMS (ES) m/z 350 (M+H)$^+$; $^1$H-NMR(MeOD) δ 1.39 (d, 2H), 1.86 (m, 1H), 1.97 (m, 2H), 2.30 (m, 4H), 2.69 (s, 3H), 2.84 (d, 2H), 3.69 (s, 2H), 7.28 (m, 2H), 7.36 (m, 8H).

Example 6

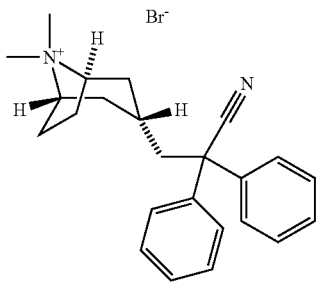

(Endo)-3-(2-cyano-2,2-diphenyl-ethyl)-8,8-dimethyl-8-azonia-bicyclo[3.2.1]octane bromide A solution of 3-((endo)-8-methyl-8-aza-bicyclo[3.2.1]oct-3-yl)-2,2-diphenyl-propionitrile (310 mg, 0.938 mmol) in acetone (6.0 mL) was mixed with MeBr (4.69 mL, 2.0 M in t-BuOMe, 9.38 mmol). The resultant mixture was stirred at room temperature for 60 minutes and filtered. The solid was washed with acetone (2×3 mL) to afford the title compound (333 mg, 83%): LCMS (ES) m/z 345 (M)$^+$; $^1$H-NMR(MeOD) δ 1.82 (d, 2H), 2.17 (m, 1H), 2.35 (m, 2H), 2.49 (m, 4H), 3.01 (d, 2H), 3.07 (s, 3H), 3.10 (s, 3H), 3.79 (s, 2H), 7.36 (m, 2H), 7.43 (m, 4H), 7.49 (m, 4H).

Example 8

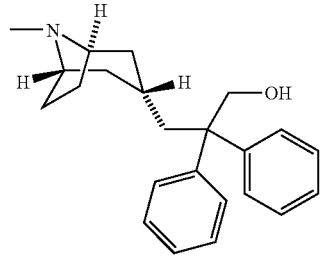

3-((Endo)-8-methyl-8-aza-bicyclo[3.2.1]oct-3-yl)-2,2-diphenyl-propan-1-ol

A mixture of 3-((endo)-8-methyl-8-aza-bicyclo[3.2.1]oct-3-yl)-2,2-diphenyl-propionic acid (42.5 mg, 0.122 mmol) and LiAlH$_4$ (0.488 mL, 1.0 M in THF, 0.488 mmol) was heated with a microwave reactor at 100° C. for 1 hour. It was diluted with saturated Na$_2$SO$_4$ solution, filtered through celite and concentrated. The resultant residue was dissolved in DMSO and filtered. Purification via a reverse phase HPLC (Gilson) then afforded the title compound (29.1 mg, 71%): LCMS (ES) m/z 336(M+H)$^+$; $^1$H-NMR(CDCl$_3$) δ 1.40 (d, 2H), 1.92 (m, 1H), 2.29 (m, 6H), 2.59 (m, 2H), 2.68 (d, 3H), 3.72 (s, 2H), 4.16 (s, 2H), 7.13 (m, 3H), 7.30 (m, 7H).

Example 7

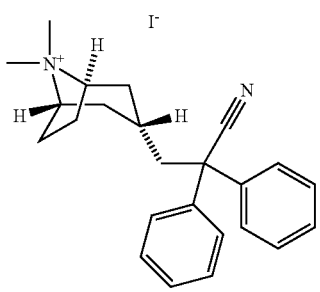

(Endo)-3-(2-cyano-2,2-diphenyl-ethyl)-8,8-dimethyl-8-azonia-bicyclo[3.2.1]octane iodide A solution of 3-((endo)-8-methyl-8-aza-bicyclo[3.2.1]oct-3-yl)-2,2-diphenyl-propionitrile (26.5 mg, 0.080 mmol) in CH$_2$Cl$_2$ (0.5 mL) and MeCN (0.5 mL) was mixed with MeI (0.125 mL, 2.00 mmol). The resultant mixture was stirred at room temperature for 3 hours, diluted with DMSO (0.3 mL) and concentrated. Purification via a reverse phase HPLC (Gilson) then afforded the title compound (22.9 mg, 60%): LCMS (ES) m/z 345 (M)$^+$; $^1$H-NMR(CDCl$_3$) δ 1.83 (d, 2H), 2.17 (m, 1H), 2.35 (m, 2H), 2.49 (m, 4H), 3.01 (d, 2H), 3.07 (s, 3H), 3.10 (s, 3H), 3.79 (s, 2H), 7.36 (m, 2H), 7.43 (m, 4H), 7.49 (m, 4H).

Example 9

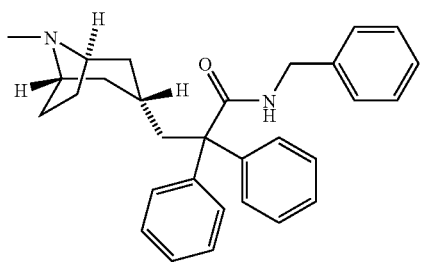

N-Benzyl-3-((endo)-8-methyl-8-aza-bicyclo[3.2.1]oct-3-yl)-2,2-diphenyl-propionamide A solution of 3-((endo)-8-methyl-8-aza-bicyclo[3.2.1]oct-3-yl)-2,2-diphenyl-propionic acid (82.0 mg, 0.235 mmol) in CH$_2$Cl$_2$ (3.0 mL) was mixed with PhCH$_2$NH$_2$ (28.2 μL, 0.258 mmol), EDC (49.5 mg, 0.258 mmol), HOBt (3.2 mg, 0.024 mmol) and (CH$_3$CH$_2$)$_3$N (0.232 mL, 1.65 mmol). The mixture was stirred at room temperature for 60 hours and concentrated. The resultant residue was dissolved in DMSO and filtered. Purification via a reverse phase HPLC (Gilson) then afforded the title compound (29.8 mg, 30%): LCMS (ES) m/z 439(M+H)$^+$; $^1$H-NMR(CDCl$_3$) δ 1.34 (d, 2H), 1.96 (m, 1H), 2.23 (m, 2H), 2.38 (m, 4H), 2.63 (d, 3H), 2.83 (d, 2H), 3.66 (s, 2H), 4.41 (s, 2H), 6.93 (m, 2H), 7.22 (m, 3H), 7.38 (m, 10H).

Example 10

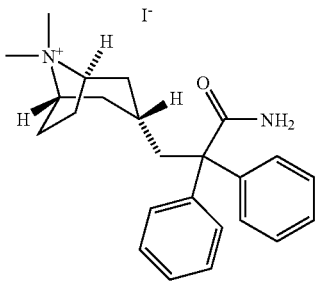

(Endo)-3-(2-carbamoyl-2,2-diphenyl-ethyl)-8,8-dimethyl-8-azonia-bicyclo[3.2.1]octane iodide The title compound was prepared from 3-((endo)-8-methyl-8-aza-bicyclo[3.2.1]oct-3-yl)-2,2-diphenyl-propionamide by following the procedure of Example 7 (33% yield): LCMS (ES) m/z 363 (M)$^+$; $^1$H-NMR(CDCl$_3$) δ 1.49 (d, 2H), 1.95 (m, 1H), 2.25 (m, 2H), 2.42 (m, 4H), 2.84 (d, 2H), 3.17 (s, 3H), 3.23 (s, 3H), 3.93 (s, 2H), 5.65 (s, 1H), 5.91 (s, 1H), 7.39 (m, 10H).

Example 11

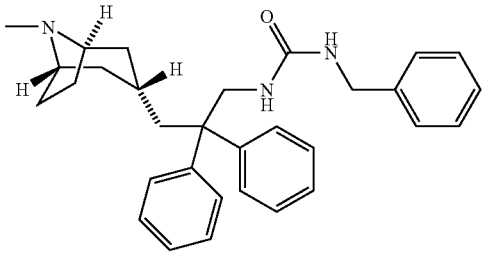

1-Benzyl-3-[3-((endo)-8-methyl-8-aza-bicyclo[3.2.1]oct-3-yl)-2,2-diphenyl-propyl]-urea

11a) 3-((Endo)-8-methyl-8-aza-bicyclo[3.2.1]oct-3-yl)-2,2-diphenyl-propylamine A solution of 3-((endo)-8-methyl-8-aza-bicyclo[3.2.1]oct-3-yl)-2,2-diphenyl-propionitrile (250 mg, 0.758 mmol) in THF (2.5 mL) was mixed with BH$_3$ (2.53 mL, 1.5 M in THF, 3.79 mmol) at 0° C. The mixture was stirred at room temperature for 20 hours and diluted with H$_2$O (1.0 mL). The solution was then mixed with K$_2$CO$_3$ (0.1 g) and stirred at room temperature for 1 hour. Organic layers were separated and the aqueous part was extracted with EtOAc (2×3 mL). The organic layers were combined, dried over Na$_2$SO$_4$ and concentrated. Purification via a reverse phase HPLC (Gilson) afforded the titled compound (159 mg, 63%): LCMS (ES) m/z 335 (M+H)$^+$; $^1$H-NMR(MeOD) δ 1.35 (d, 2H), 2.01 (m, 3H), 2.34 (s, 4H), 2.55 (s, 2H), 2.68 (s, 3H), 3.73 (m, 5H), 7.26 (m, 4H), 7.33 (m, 2H), 7.43 (m, 4H).

11b) 1-Benzyl-3-[3-((endo)-8-methyl-8-aza-bicyclo[3.2.1]oct-3-yl)-2,2-diphenyl-propyl]-urea A solution of 3-((endo)-8-methyl-8-aza-bicyclo[3.2.1]oct-3-yl)-2,2-diphenyl-propylamine (50.0 mg, 0.149 mmol) in CH$_2$Cl$_2$ (2.0 mL) was mixed with PhCH$_2$NCO (20.4 µL, 0.164 mmol) and (CH$_3$CH$_2$)$_3$N (62.8 µL, 0.447 mmol). The result mixture was stirred at room temperature for 1 hours and concentrated. Purification via a reverse phase HPLC (Gilson) then afforded the titled compound (13.0 mg, 19%): LCMS (ES) m/z 468 (M+H)$^+$; $^1$H-NMR(MeOD) δ 1.24 (d, 2H), 1.94 (m, 3H), 2.25 (m, 4H), 2.49 (d, 2H), 2.67 (s, 3H), 3.62 (s, 2H), 3.97 (s, 2H), 4.23 (s, 2H), 7.22 (m, 6H), 7.33 (m, 4H).

Example 12

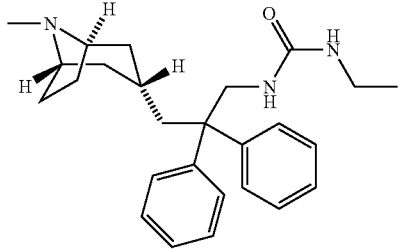

1-Ethyl-3-[3-((endo)-8-methyl-8-aza-bicyclo[3.2.1]oct-3-yl)-2,2-diphenyl-propyl]-urea The title compound was prepared from 3-((endo)-8-methyl-8-aza-bicyclo[3.2.1]oct-3-yl)-2,2-diphenyl-propylamine and CH$_3$CH$_2$NCO by following the procedure in Example 11 (45% yield): LCMS (ES) m/z 406 (M+H)$^+$; $^1$H-NMR(MeOD) δ 1.03 (t, 3H), 1.33 (d, 2H), 1.94 (m, 3H), 2.25 (m, 4H), 2.55 (d, 2H), 2.67 (s, 3H), 3.07 (q, 2H), 3.68 (s, 2H), 3.94 (s, 2H), 7.24 (m, 6H), 7.34 (m, 4H).

Example 13

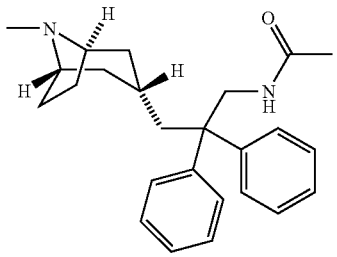

N-[3-((Endo)-8-methyl-8-aza-bicyclo[3.2.1]oct-3-yl)-2,2-diphenyl-propyl]-acetamide A solution of 3-((endo)-8-methyl-8-aza-bicyclo[3.2.1]oct-3-yl)-2,2-diphenyl-propylamine (33.4 mg, 0.10 mmol) in CH$_2$Cl$_2$ (0.5 mL) was mixed with Ac$_2$O (18.9 µL, 0.20 mmol) and pyridine (16.2 µL, 0.20 mmol). The mixture was stirred at room temperature for 1 hour and concentrated. Purification via a reverse phase HPLC (Gilson) then afforded the title compound (10.7 mg, 29%): LCMS (ES) m/z 377 (M+H)$^+$; $^1$H-NMR(MeOD) δ 1.26 (d, 2H), 1.82 (s, 3H), 1.96 (m, 3H), 2.26 (s, 4H), 2.53 (d, 2H), 2.67 (s, 3H), 3.66 (s, 2H), 4.00 (s, 2H), 7.24 (m, 6H), 7.33 (m, 4H).

Example 14

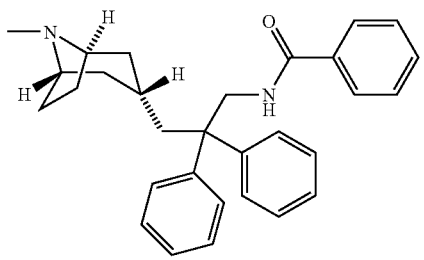

N-[3-((Endo)-8-methyl-8-aza-bicyclo[3.2.1]oct-3-yl)-2,2-diphenyl-propyl]-benzamide The title compound was prepared from 3-((endo)-8-methyl-8-aza-bicyclo[3.2.1]oct-3-yl)-2,2-diphenyl-propylamine and (PhCO)$_2$O by following the procedure in Example 13 (8% yield): LCMS (ES) m/z 439 (M+H)$^+$; $^1$H-NMR(MeOD) δ 1.28 (d, 2H), 2.00 (m, 3H), 2.24 (s, 4H), 2.59 (d, 2H), 2.67 (s, 3H), 3.65 (s, 2H), 4.21 (s, 2H), 7.31 (m, 6H), 7.39 (m, 6H), 7.50 (m, 3H).

Example 15

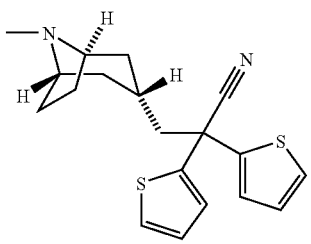

3-((Endo)-8-methyl-8-aza-bicyclo[3.2.1]oct-3-yl)-2,2-di-thiophen-2-yl-propionitrile The title compound was prepared from (endo)-3-iodomethyl-8-methyl-8-aza-bicyclo[3.2.1]octane and 2,2-di-thiophen-2-yl-acetonitrile by following the procedure in Example 2C (34% yield): LCMS (ES) m/z 343 (M+H)$^+$; $^1$H-NMR(CDCl$_3$) δ 1.79 (m, 2H), 2.21 (m, 2H), 2.33 (m, 2H), 2.62 (m, 2H), 2.73 (m, 4H), 3.80 (m, 2H), 4.35 (s, 2H), 7.02 (m, 2H), 7.23 (m, 2H), 7.37 (m, 2H).

Example 16

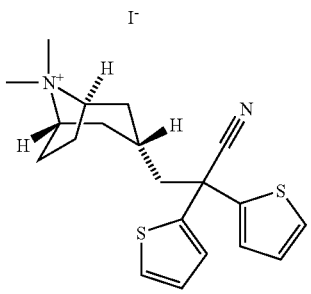

(Endo)-3-(2-cyano-2,2-di-thiophen-2-yl-ethyl)-8,8-dimethyl-8-azonia-bicyclo[3.2.1]octane iodide The title compound was prepared from 3-((endo)-8-methyl-8-aza-bicyclo[3.2.1]oct-3-yl)-2,2-di-thiophen-2-yl-propionitrile by following the procedure in Example 7 (43%): LCMS (ES) m/z 345 (M)$^+$; $^1$H-NMR(CDCl$_3$) δ 1.82 (d, 2H), 2.35 (m, 2H), 2.23 (m, 3H), 2.58 (m, 4H), 2.82 (m, 2H), 3.37 (s, 6H), 4.25 (s, 2H), 7.02 (m, 2H), 7.24 (m, 2H), 7.36 (m, 2H).

Example 17

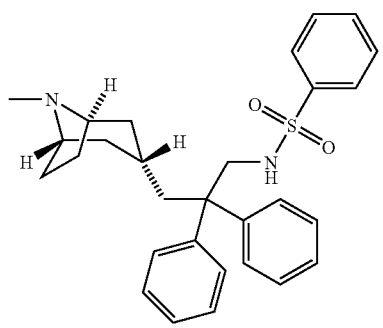

N-[3-((Endo)-8-methyl-8-aza-bicyclo[3.2.1]oct-3-yl)-2,2-diphenyl-propyL]-benzenesulfonamide A solution of 3-((endo)-8-methyl-8-aza-bicyclo[3.2.1]oct-3-yl)-2,2-diphenyl-propylamine (67.0 mg, 0.20 mmol) in CH$_2$Cl$_2$ (2.0 mL) was mixed with PhSO$_2$Cl (28.2 μL, 0.22 mmol) and (CH$_3$CH$_3$)$_3$N (84.3 μL, 0.60 mmol). The result mixture was stirred at room temperature for 1 hours and concentrated. Purification via a reverse phase HPLC (Gilson) then afforded the title compound (51.5 mg, 54%): LCMS (ES) m/z 475 (M+H)$^+$; $^1$H-NMR(MeOD) δ 1.39 (d, 2H), 2.01 (m, 3H), 2.30 (s, 4H), 2.69 (s, 5H), 3.60 (s, 2H), 3.68 (s, 2H), 7.12 (m, 4H), 7.27 (m, 6H), 7.55 (m, 2H), 7.63(m, 1H), 7.78 (m, 2H).

Example 18

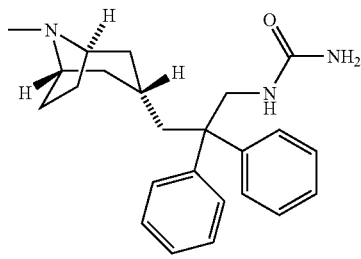

[3-((Endo)-8-methyl-8-aza-bicyclo[3.2.1]oct-3-yl)-2,2-diphenyl-propyl]-urea

To a solution of 3-((endo)-8-methyl-8-aza-bicyclo[3.2.1]oct-3-yl)-2,2-diphenyl-propylamine (50.0 mg, 0.149 mmol) in CH$_2$Cl$_2$ (4.0 mL), ClSO$_2$NCO (31.2 μL, 0.358 mmol) was added. The mixture was stirred at room temperature for 2 days and concentrated. Purification via a reverse phase HPLC (Gilson) then afforded the title compound (21.6 mg, 38%): LCMS (ES) m/z 378 (M+H)$^+$; $^1$H-NMR(MeOD) δ 1.33 (d, 2H), 2.01 (m, 3H), 2.29 (s, 4H), 2.57 (m, 2H), 2.68 (s, 3H), 3.69 (s, 2H), 4.01 (s, 2H), 7.25 (m, 6H), 7.34 (m, 4H).

Example 19

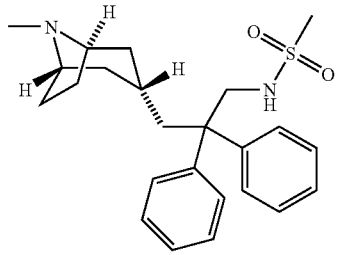

N-[3-((Endo)-8-methyl-8-aza-bicyclo[3.2.1]oct-3-yl)-2,2-diphenyl-propyl]-methanesulfonamide The title compound was prepared from 3-((endo)-8-methyl-8-aza-bicyclo[3.2.1]oct-3-yl)-2,2-diphenyl-propylamine and MeSO$_2$Cl by following the procedure in Example 17 (28% yield): LCMS (ES) m/z 413 (M+H)$^+$; $^1$H-NMR(MeOD) δ 1.39 (d, 2H), 1.97 (m, 3H), 2.30 (s, 4H), 2.68 (s, 3H), 2.76 (s, 3H), 3.68 (s, 2H), 3.84 (s, 2H), 7.23 (s, 6H), 7.33 (s, 4H).

Example 20

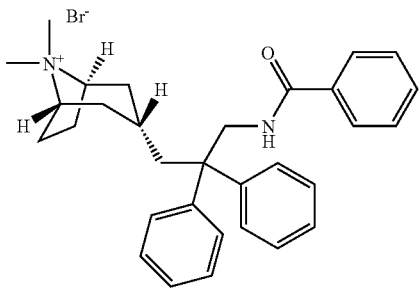

(Endo)-3-{2,2-diphenyl-3-[(1-phenyl-methanoyl)-amino]-propyl}-8,8-dimethyl-8-azonia-bicyclo[3.2.1]octane bromide A solution of N-[3-((endo)-8-methyl-8-aza-bicyclo[3.2.1]oct-3-yl)-2,2-diphenyl-propyl]-benzamide (29 mg, 0.0683 mmol) in CH$_2$Cl$_2$ (0.5 mL) and acetone (0.5 mL) was mixed with MeBr (0.342 mL, 2.0 M in t-butyl methyl ether, 0.683 mmol). The resultant mixture was stirred at room temperature for 3 hours and concentrated. Purification via a reverse phase HPLC (Gilson) then afforded the title compound (19.6 mg, 64%): LCMS (ES) m/z 453 (M)$^+$; $^1$H-NMR(MeOD) δ 1.20 (d, 2H), 2.32 (m, 7H), 2.65 (d, 2H), 2.98 (s, 3H), 3.02 (s, 3H), 3.60 (s, 2H), 4.22 (s, 2H), 7.30(m, 6H), 7.39(m, 6H), 7.50 (s, 3H).

BIOLOGICAL EXAMPLES

The inhibitory effects of compounds at the M$_3$ mAChR of the present invention are determined by the following in vitro and in vivo assay:

Analysis of Inhibition of Receptor Activation by Calcium Mobilization:

Stimulation of mAChRs expressed on CHO cells were analyzed by monitoring receptor-activated calcium mobilization as previously described[10]. CHO cells stably expressing M$_3$ mAChRs were plated in 96 well black wall/clear bottom plates. After 18 to 24 hours, media was aspirated and replaced with 100 μl of load media (EMEM with Earl's salts, 0.1% RIA-grade BSA (Sigma, St. Louis Mo.), and 4 μM Fluo-3-acetoxymethyl ester fluorescent indicator dye (Fluo-3 AM, Molecular Probes, Eugene, Oreg.) and incubated 1 hr at 37° C. The dye-containing media was then aspirated, replaced with fresh media (without Fluo-3 AM), and cells were incubated for 10 minutes at 37° C. Cells were then washed 3 times and incubated for 10 minutes at 37° C. in 100 μl of assay buffer (0.1% gelatin (Sigma), 120 mM NaCl, 4.6 mM KCl, 1 mM KH$_2$ PO$_4$, 25 mM NaH CO$_3$, 1.0 mM CaCl$_2$, 1.1 mM MgCl$_2$, 11 mM glucose, 20 mM HEPES (pH 7.4)). 50 μl of compound (1×10$^{-11}$-1×10$^{-5}$ M final in the assay) was added and the plates were incubated for 10 min. at 37° C. Plates were then placed into a fluorescent light intensity plate reader (FLIPR, Molecular Probes) where the dye loaded cells were exposed to excitation light (488 nm) from a 6 watt argon laser. Cells were activated by adding 50 μl of acetylcholine (0.1-10 nM final), prepared in buffer containing 0.1% BSA, at a rate of 50 μl/sec. Calcium mobilization, monitored as change in cytosolic calcium concentration, was measured as change in 566 nm emission intensity. The change in emission intensity is directly related to cytosolic calcium levels[11]. The emitted fluorescence from all 96 wells is measured simultaneously using a cooled CCD camera. Data points are collected every second. This data was then plotting and analyzed using GraphPad PRISM software.

Methacholine-Induced Bronchoconstriction

Airway responsiveness to methacholine was determined in awake, unrestrained BalbC mice (n=6 each group). Barometric plethysmography was used to measure enhanced pause (Penh), a unitless measure that has been shown to correlate with the changes in airway resistance that occur during bronchial challenge with methacholine[12]. Mice were pretreated with 50 μl of compound (0.003-10 μg/mouse) in 50 μl of vehicle (10% DMSO) intranasally, and were then placed in the plethysmography chamber. Once in the chamber, the mice were allowed to equilibrate for 10 min before taking a baseline Penh measurement for 5 minutes. Mice were then challenged with an aerosol of methacholine (10 mg/ml) for 2 minutes. Penh was recorded continuously for 7 min starting at the inception of the methacholine aerosol, and continuing for 5 minutes afterward. Data for each mouse were analyzed and plotted by using GraphPad PRISM software.

What is claimed is:

1. A compound having structure II provided that R2 and R3 are not 2-thiophene when R4 is —OC(O)CH$_3$;

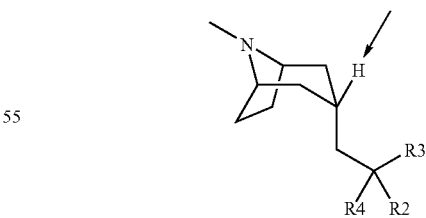

II wherein:
the H atom indicated is in the exo position;
R2 and R3 are independently selected from the group consisting of straight or branched chain lower alkyl groups (having from 1 to 6 carbon atoms), cycloalkyl groups (having from 5 to 6 carbon atoms), aryl, and heteroaryl;

R4 is selected from the group consisting of $(C_1-C_6)$alkyl, $(C_3-C_{12})$cycloalkyl, $(C_1-C_6)$alkyl$(C_3-C_{12})$cycloalkyl, aryl, heteroaryl, $(C_1-C_6)$alkyl-aryl, $(C_1-C_6)$alkyl-heteroaryl, —OR5, —CH$_2$OR5, —CH$_2$OH, —CN, —CF$_3$, —CH$_2$O(CO)R6, —CO$_2$R7, —CH$_2$NH$_2$, —CH$_2$N(R7)SO$_2$R5, —SO$_2$N(R7)(R8), —CON(R7)(R8), —CH$_2$N(R8)CO(R6), —CH$_2$N(R8)SO$_2$(R6), —CH$_2$N(R8)CO$_2$(R5), and —CH$_2$N(R8)CONH(R7);

R5 is selected from the group consisting of $(C_1-C_6)$alkyl, $(C_1-C_6)$alkyl$(C_3-C_{12})$cycloalkyl, $(C_1-C_6)$alkyl-aryl, $(C_1-C_6)$alkyl heteroaryl;

R6 is selected from the group consisting of $(C_1-C_6)$alkyl, $(C_3-C_{12})$cycloalkyl, $(C_1-C_6)$alkyl$(C_3-C_{12})$cycloalkyl, aryl, heteroaryl, $(C_1-C_6)$alkyl-aryl, $(C_1-C_6)$alkyl-heteroaryl;

R7 and R8 are, independently, selected from the group consisting of hydrogen, $(C_1-C_6)$alkyl, $(C_3-C_{12})$cycloalkyl, $(C_1-C_6)$alkyl$(C_3-C_{12})$cycloalkyl, $(C_1-C_6)$alkyl-aryl, and $(C_1-C_6)$alkyl heteroary.

2. The compound according to claim 1 wherein
R2 and R3 are independently selected from the group consisting of aryl, or heteroaryl;
R4 is selected from the group consisting of aryl, OR5, CH$_2$OR5, CH$_2$OH, CN, CO$_2$R7, CH$_2$N(R7)SO$_2$R5, CONR7R8, CH$_2$N(R8)CO(R6), CH$_2$N(R8) SO$_2$(R6), CH$_2$N(R8)CO$_2$(R5), CH$_2$N(R8)CONH(R7);
R5 is a $(C_1-C_6)$alkyl;
R6 is selected from the group consisting of $(C_1-C_6)$alkyl or aryl; and
R7 and R8 independently selected from the group consisting of hydrogen, or $(C_1-C_6)$alkyl.

3. The compound according to claim 1 wherein R2 and R3 are independently selected from the group consisting of aryl, or heteroaryl.

4. The compound according to claim 3 wherein R2 and R3 are both aryl.

5. The compound according to claim 4 wherein R2 and R3 are both phenyl.

6. The compound according to claim 5 wherein R4 is cyano.

7. The compound according to claim 2 wherein R2 and R3 are both aryl.

8. The compound according to claim 7 wherein R2 and R3 are both phenyl.

9. The compound according to claim 8 wherein R4 is cyano.

10. The compound according to claim 2 wherein R4 is cyano.

11. The compound according to claim 3 wherein R2 and R3 are both heteroaryl.

12. The compound according to claim 11 wherein R2 and R3 are both thienyl.

13. The compound according to claim 2 wherein R2 and R3 are both heteroaryl.

14. The compound according to claim 13 wherein R2 and R3 are both thienyl.

15. The compound according to claim 2 wherein R4 is CONR7R8.

16. The compound according to claim 15 wherein R7 and R8 are both hydrogen.

17. The compound according to claim 2 wherein —CH$_2$N(R8)SO$_2$(R6) and R6 is aryl.

18. The compound according to claim 2 wherein R4 is —CH$_2$N(R8)CO(R6), and R6 is aryl or $(C_1-C_6)$alkyl.

19. The compound according to claim 2 wherein R4 is OR5, CH$_2$OR5, and CH$_2$OH.

20. The compound according to claim 19 wherein R5 is methyl.

21. The compound according to claim 2 wherein R4 is CO$_2$R7, and R7 is hydrogen.

22. The compound according to claim 2 wherein R4 is CH$_2$N(R7)SO$_2$R5 and R5 is methyl.

23. The compound according to claim 2 wherein R4 is CH$_2$N(R8)CO(R6), R8 is hydrogen, and R6 is aryl.

24. The compound according to claim 2 wherein R4 is CH$_2$N(R8)CONH(R7), R8 is hydrogen, and the R7 is $(C_1-C_6)$alkyl.

25. The compound according to claim 2 wherein R4 is CH$_2$N(R8)CONH(R7), and R7 and R8 are both hydrogen.

26. The compound according to claim 1 which is:
3-((Endo)-8-methyl-8-aza-bicyclo[3.2.1]oct-3-yl)-2,2-diphenyl-propionitrile;
(Endo)-8-methyl-3-(2,2,2-triphenyl-ethyl)-8-aza-bicyclo[3.2.1]octane;
3-((Endo)-8-methyl-8-aza-bicyclo[3.2.1]oct-3-yl)-2,2-diphenyl-propionamide;
3-((Endo)-8-methyl-8-aza-bicyclo[3.2.1]oct-3-yl)-2,2-diphenyl-propionic acid;
3-((Endo)-8-methyl-8-aza-bicyclo[3.2.1]oct-3-yl)-2,2-diphenyl-propan-1-ol;
1-Ethyl-3-[3-((endo)-8-methyl-8-aza-bicyclo[3.2.1]oct-3-yl)-2,2-diphenyl-propyl]-urea;
N-[3-((Endo)-8-methyl-8-aza-bicyclo[3.2.1]oct-3-yl)-2,2-diphenyl-propyl]-acetamide;
N-[3-((Endo)-8-methyl-8-aza-bicyclo[3.2.1]oct-3-yl)-2,2-diphenyl-propyl]-benzamide;
3-((Endo)-8-methyl-8-aza-bicyclo[3.2.1]oct-3-yl)-2,2-dithiophen-2-yl-propionitrile;
N-[3-((Endo)-8-methyl-8-aza-bicyclo[3.2.1]oct-3-yl)-2,2-diphenyl-propyl]-benzenesulfonamide;
[3-((Endo)-8-methyl-8-aza-bicyclo[3.2.1]oct-3-yl)-2,2-diphenyl-propyl]-urea; and
N-[3-((Endo)-8-methyl-8-aza-bicyclo[3.2.1]oct-3-yl)-2,2-diphenyl-propyl]-methanesulfonamide.

27. The compound which is 3-((Endo)-8-methyl-8-aza-bicyclo[3.2.1]oct-3-yl)-2,2-diphenyl-propionitrile.

28. A pharmaceutical composition comprising a compound according to claim 1 and a pharmaceutically acceptable carrier or diluent.

29. A pharmnaceutical composition comprising a compound according to claim 2 and a pharmnaceutically acceptable carrier or diluent.

30. A pharmaceutical composition comprising a compound according to claim 26 and a pharmaceutically acceptable carrier or diluent.

31. A pharmaceutical composition comprising a compound according to claim 27 and a pharmnaceutically acceptable carrier or diluent.

32. A pharmnaceutical composition comprising 3-((Endo)-8-methyl-8-aza-bicyclo[3.2.1]oct-3-yl)-2,2-diphenyl-propionitrile and a pharmnaceutically acceptable carrier or diluent.

* * * * *